(12) United States Patent
Robinson

(10) Patent No.: US 7,601,156 B2
(45) Date of Patent: Oct. 13, 2009

(54) LIMB LENGTHENER

(75) Inventor: Randolph C. Robinson, 7144 S. Chapparm Cir. E., Lone Tree, CO (US) 80124

(73) Assignee: Randolph C. Robinson, Centennial, CO (US)

( * ) Notice: Subject to any disclaimer, the term of this patent is extended or adjusted under 35 U.S.C. 154(b) by 681 days.

(21) Appl. No.: 10/306,857

(22) Filed: Nov. 27, 2002

(65) Prior Publication Data
US 2003/0144669 A1    Jul. 31, 2003

Related U.S. Application Data

(60) Provisional application No. 60/337,580, filed on Dec. 5, 2001.

(51) Int. Cl.
*A61B 17/58* (2006.01)
*A61F 2/00* (2006.01)

(52) U.S. Cl. .......................... 606/90; 606/105
(58) Field of Classification Search ............ 606/60, 606/90, 54, 57, 105, 53, 58, 59, 63, 56, 68, 606/86 R
See application file for complete search history.

(56) References Cited

U.S. PATENT DOCUMENTS

| | | | |
|---|---|---|---|
| 3,976,060 A | | 8/1976 | Hildebrandt et al. |
| 3,985,127 A | * | 10/1976 | Volkov et al. ............... 606/90 |
| 3,993,055 A | * | 11/1976 | Volkov et al. ............... 606/90 |
| 4,011,602 A | | 3/1977 | Rybicki et al. |
| 4,096,857 A | | 6/1978 | Cramer et al. |
| 4,244,360 A | | 1/1981 | Dohogne |
| 4,535,763 A | * | 8/1985 | Jaquet ........................ 606/56 |
| 4,682,951 A | | 7/1987 | Linkow |
| 4,744,753 A | | 5/1988 | Ross |
| 4,744,853 A | | 5/1988 | Landua et al. |
| 4,886,456 A | | 12/1989 | Ross |
| 4,889,111 A | * | 12/1989 | Ben-Dov ...................... 606/56 |

(Continued)

FOREIGN PATENT DOCUMENTS

EP    0791337 A    8/1997

(Continued)

OTHER PUBLICATIONS

Schollner, D., New ways of operating to lengthen the femur, Z. Orthop. 110:971-974 (1972).

(Continued)

*Primary Examiner*—Pedro Philogene
(74) *Attorney, Agent, or Firm*—Cooley Godward Kronish LLP

(57) ABSTRACT

A bone distraction device and a method for installing and using the bone distraction device are disclosed. Separated portions of a bone may be coupled to two or more mounts of the bone distraction device. Each portion of the bone may be coupled to at least one mount. The mounts may be contoured in arcs of at least π/3 radians to accommodate the circumference of the bone. The bone distraction device may include three or more guide rods coupled to the mounts. A distractor may be used to move one mount relative to one or more other mounts to distract the bone portions. In one embodiment, one mount may be coupled to a transport segment of bone for transport distraction between two bone segments. In some embodiments, a hydraulic bone distractor may be used to distract the bone portions.

77 Claims, 11 Drawing Sheets

U.S. PATENT DOCUMENTS

| | | | |
|---|---|---|---|
| 4,906,191 A | | 3/1990 | Soderberg |
| 4,929,247 A | | 5/1990 | Rayhack |
| 4,978,348 A | | 12/1990 | Ilizarov |
| 5,062,844 A | * | 11/1991 | Jamison et al. ............... 606/54 |
| 5,066,224 A | | 11/1991 | Block et al. |
| 5,129,903 A | | 7/1992 | Luhr et al. |
| 5,156,605 A | | 10/1992 | Pursley et al. |
| 5,320,529 A | | 6/1994 | Pompa |
| 5,364,396 A | * | 11/1994 | Robinson et al. .............. 606/53 |
| 5,489,210 A | | 2/1996 | Hanosh |
| 5,611,688 A | | 3/1997 | Hanosh |
| 5,725,377 A | | 3/1998 | Lemler et al. |
| 5,885,282 A | * | 3/1999 | Szabo ......................... 606/56 |
| 6,050,819 A | | 4/2000 | Robinson |
| 6,245,075 B1 | * | 6/2001 | Betz et al. ................... 606/105 |
| 6,383,189 B1 | * | 5/2002 | Schumacher .............. 606/86 R |
| 6,752,808 B2 | * | 6/2004 | Schumacher ................. 606/90 |

FOREIGN PATENT DOCUMENTS

| | | |
|---|---|---|
| EP | 0832613 A1 | 4/1998 |
| EP | 0832613 B1 | 4/1998 |
| WO | WO 98/09577 | 3/1998 |

OTHER PUBLICATIONS

Anderson, W. V. Leg Lengthening, *J. Bone Joint Surg.* [Br] 34-b:150 (1952).

Verkerke, G. J., Koops, H.S., Verb. R.P.H., Nielsen, H.K.L., Design of a load cell for the Wagner distractor, *Proc. Instn. Mech. Engrs.* 203:91-96 (1989).

Witt, A.N., Jager, M., Bruns, H., Kusswetter, W., Hildebrant, J.J., Die operative Oberschenkelverlangerung mit einem vollimplantierbaren Distraktionsgerat, *Arch. Orthop. Traumat. Surg.* 92:291-296 (1978).

Hellend, P., Femoral elongation by use of an elongable intramedullary device, *Acta Orthop. Scand.* 63(Suppl. 247):16 (1992).

Baumann, F., Harms, J., The extension nail. A new method for lengthening of the femur and tibia, *Arch. Orthop. Unfall-Chir.* 90:139-146 (1977).

Gotz, J., Schellmann, W.D., Continuous lengthening of the femur with intramedullary stabilization, *Arch. Orthop. Unfall-Chir.* 82:305-310 (1975).

Herzenberg, J. E., Hensinger, R.N., Goldstein, S.A., Michigan Intramedullary Leg Lengthening Nail, in: Biomechanics, Trauma and Sports Medicine Laboratory Annual Report, University of Michigan (1989).

* cited by examiner

LIMB LENGTHENER

PRIORITY CLAIM

This application claims priority to U.S. Provisional Application No. 60/337,580 entitled "Limb Lengthener," filed Dec. 5, 2001. The above-referenced provisional application is hereby incorporated by reference as if fully set forth herein.

BACKGROUND OF THE INVENTION

1. Field of the Invention

The present invention relates generally to devices and procedures used during orthopedic surgery. An embodiment relates to bone lengthening by distraction osteogenesis.

2. Description of Related Art

Some people may have one or more shortened limbs due to short bone length in the affected limbs. Short bone lengths may be due to birth defects, disease, and/or injury. Distraction osteogenesis may be used to elongate a short bone. Distraction osteogenesis may involve a separation phase, an activation phase, and a consolidation phase. During the separation phase, a bone that is to be elongated may be cut at a selected location to separate the bone into two pieces. The bone pieces may be stabilized relative to each other with a separation mechanism. A callus may form between the ends of the two bone pieces. During the activation phase, the bone pieces may be gradually separated using a separation mechanism. The separation mechanism may separate the bone pieces at a rate of approximately 1 millimeter (mm) per day. Gradual separation of the bone pieces may result in slow stretching of the callus. Slow stretching of the callus may result in the formation of additional callus at an interface between the bone pieces. In addition, gradual stretching of the callus may allow neurovascular bundles and muscles to adjust in position and/or length. After a desired length of the bone is obtained, separation of the bone pieces may be stopped. A consolidation phase may ensue. During the consolidation phase, the separation mechanism may be left in position to provide support to the forming bone and remaining portions of callus.

Distraction osteogenesis was pioneered by the Soviet orthopedic surgeon Dr. Gavriel Ilizarov. Ilizarov lengthened the limbs of dwarfs up to eighteen inches using bicycle sprockets and spokes to form extendable cages fitting externally over the patient's limbs. The distal end of the cage was incrementally extended from the proximal portion mechanically. A plurality of pins was inserted through the muscle of the limb, and into both portions of the bone. With the proximal portion of the limb "anchored" by the pins in the cage, force was transmitted through the pins to pull the distal portion away from the anchored portion. This type of device required numerous incisions in a limb for the pins. The incisions were susceptible to infection and the pins were continually pulling on flesh. Furthermore, wearing a cage over a period of months severely limited the mobility of the patient.

Various distracting means have been developed, such as external fixators, in which each segment of bone is transfixed by pins or wires coupled to clamps, which are then distracted. Examples of external fixator systems include: (i) bilateral frames, for which fixator bodies or rods are located one on each side of the bone being transfixed, (ii) unilateral frames, for which only a single fixator body or rod is located to one side of the bone, and (iii) ring fixators, for which a series of rings are spatially arranged around the limbs so as to form a cylinder, the rings being interconnected by struts.

The applications of lengthening procedures using external fixators have been limited due to a high rate of complications, including wire site infection, bone infection, pain, scarring, patient discomfort, and restricted joint motion due to the transfixation of tendons and muscles.

Many of the associative complications with external distraction devices, such as external fixators, were eliminated when internal distraction devices were introduced. Schollner reported using a distraction device implanted adjacent to the bone being lengthened. (Schollner, D., New ways of operating to lengthen the femur, *Z. Orthop.* 110:971-974 (1972) citing Anderson, W. V., Leg lengthening, *J. Bone Joint Surg.* [Br] 34-b:150 (1952)). Gotz and Schellmann described studies on a hydraulic distractor placed in a modified interlocking nail. (Gotz, J., Schellmann, W. D., Continuous lengthening of the femur with intramedullary stabilization, *Arch. Orthop. Unfall-Chir.* 82:305-310 (1975)). According to Gotz and Schellmann, a cylinder external to the bone supplied hydraulic pressure to an internal nail. Baumann and Harms reported using a telescoping nail driven by a threaded spindle transcutaneously attached to the nail. (Baumann, F., Harms, J., The extension nail. A new method for lengthening of the femur and tibia, *Arch. Orthop. Unfall-Chir.* 90:139-146 (1977)).

Witt et al. were the first to report human clinical results from a completely implantable femur distractor. (Witt, A. N., Jager, M., Bruns, H., Kusswetter, W., Hildebrant, J. J., Die operative Oberschenkelverlangerung mit einem vollimplantierbaren Distraktionsgerat, *Arch. Orthop. Traumat. Surg.* 92:291-296 (1978)). Witt et al. reported implanting a device in the soft tissue adjacent to the bone and screwing the device into the femur proximally and distally. Witt et al. used an electric motor housed in the device to generate a distraction force. The motor is controlled by telemetry from outside the body, providing for both forward and backward motion.

Betz et al. disclosed a fully implantable intramedullary system for lengthening bones, using telemetry to control an electric motor in U.S. Pat. No. 6,245,075. Betz et al. developed two variants of an intramedullary nail, one with implanted energy and control units, and one with external energy and control units. The first device utilizes a battery pack and a telemetry receiver, which are both implanted subcutaneously, with an automatic controller. The second device uses only a receiver that is implanted and connected to the driving motor, allowing for a much smaller subcutaneous packet. The patient attaches a telemetry sender to his leg during the night, which activates the device and transmits the energy to the motor. According to the teachings of Betz et al., both devices use an electric motor to provide a distraction force.

Pursley disclosed two embodiments of an intramedullary telescoping distractor in U.S. Pat. No. 5,156,605. Like the device of Betz et al., both embodiments require a distraction force be provided using an electric motor and controller to drive a lead screw. According to the first embodiment, the motor is housed outside the body and connected to the internal tube by means of a flexible shaft. In the second embodiment, the motor and control units are internally mounted and controlled by a communication assembly from outside the body.

Other limited reports of work on internal lengthening devices include Herzenberg, J. E., Hensinger, R. N., Goldstein, S. A., Michigan intramedullary leg lengthening nail, in: *Biomechanics, Trauma and Sports Medicine Laboratory Annual Report*, University of Michigan (1989); Verkerke, G. J., Koops, H. S., Verb, R. P. H., Nielsen, H. K. L., Design of a load cell for the Wagner distractor, *Proc. Instn. Mech. Engrs.* 203:91-96 (1989); Fisher, C., personal communication., Feb.

12, 1992; and Hellend, P., Femoral elongation by use of an elongable intramedullary device, *Acta Orthop. Scand.* 63(Suppl. 247):16 (1992).

An implantable distraction device designed for a long bone may provide the capability of: (1) a low profile around the bone, (2) structural stability when attached to the bone to prevent bending movement, (3) an economical construction, and (4) distraction without the risk of infection by percutaneous wounds or significant scarring.

SUMMARY OF THE INVENTION

A bone distraction device (limb lengthener) may be used to provide gradual distraction between separate bone segments. The bone distraction device may include a first mount and a second mount. The first and second mounts may be contoured to accommodate the circumference of the bone to be lengthened. The first and second mounts may be coupled to segments of the bone using fasteners. In some embodiments, the bone may be predrilled and/or tapped to accommodate the fasteners.

A surgical corticotomy, osteotomy, or similar procedure may be performed to cut and form bone segments. The bone segments may be distracted by the bone distraction device. The bone distraction device may gradually distract the bone segments, thus encouraging or promoting new bone growth in the space between the separated bone segments. One mount of the bone distraction may move relative to the other mount and parallel to a distraction vector. The distraction of bone segments may continue until a desired separation distance is obtained.

In an embodiment, the device includes one or more guide rods. Each guide rod may have a first end and a second end. First ends of the guide rods may be coupled to the first mount. Second ends of the guide rods may be coupled to the second mount. In some embodiments, the second ends of the guide rods may be slidably engaged in openings of the second mount. The guide rods may maintain alignment between the first and second mounts as the spacing between the units is adjusted during distraction.

In an embodiment, a third mount may be used to transport a bone portion between a first bone segment and a second bone segment. A bone portion may be used to lengthen a bone where a large initial gap between the segments has been created by trauma and/or infection. The bone portion may be coupled to the third mount and positioned against a bone segment coupled to the first mount. The bone distraction device may be activated to distract the bone portion from the first bone segment coupled to the first mount towards the second bone segment coupled to the second mount. Callus may grow in the gap between the first bone segment and the bone portion. The bone portion may be distracted until compressed against the second bone segment. The bone portion may osteointegrate to the second bone segment coupled to the second mount.

In an embodiment, a hydraulic bone distractor may be used to distract bone segments. In certain embodiments, the hydraulic bone distractor may be contoured in an arc to accommodate the circumference of the bone to be distracted. A hydraulic bone distractor may include a hydraulic housing. The hydraulic housing may be coupled to a first portion of a bone. A piston may be at least partially enclose in the hydraulic housing. The piston may be coupled to a second portion of the bone. In an embodiment, the piston may move relative to the hydraulic housing to distract the second portion of the bone from the first portion of the bone. A hydraulic fluid may be provided into the hydraulic housing to move the piston relative to the hydraulic housing. In an embodiment, the hydraulic fluid may be provided from a pump coupled to the hydraulic housing. In certain embodiments, a valve may be used to inhibit backflow of hydraulic fluid towards the pump. In some embodiments, the hydraulic bone distractor may include bioabsorbable materials.

In one embodiment, the hydraulic bone distractor may include an intermediate hydraulic cylinder. The intermediate hydraulic cylinder may enclose a portion of the piston. Hydraulic fluid provided to the hydraulic housing may cause the intermediate hydraulic cylinder to move relative to the hydraulic housing. The piston may move relative to the intermediate hydraulic cylinder and the hydraulic housing. Using an intermediate hydraulic cylinder may increase the distraction distance for a hydraulic bone distractor.

BRIEF DESCRIPTION OF THE DRAWINGS

Advantages of the present invention will become apparent to those skilled in the art with the benefit of the following detailed description of the preferred embodiments and upon reference to the accompanying drawings in which.

Figure 1:
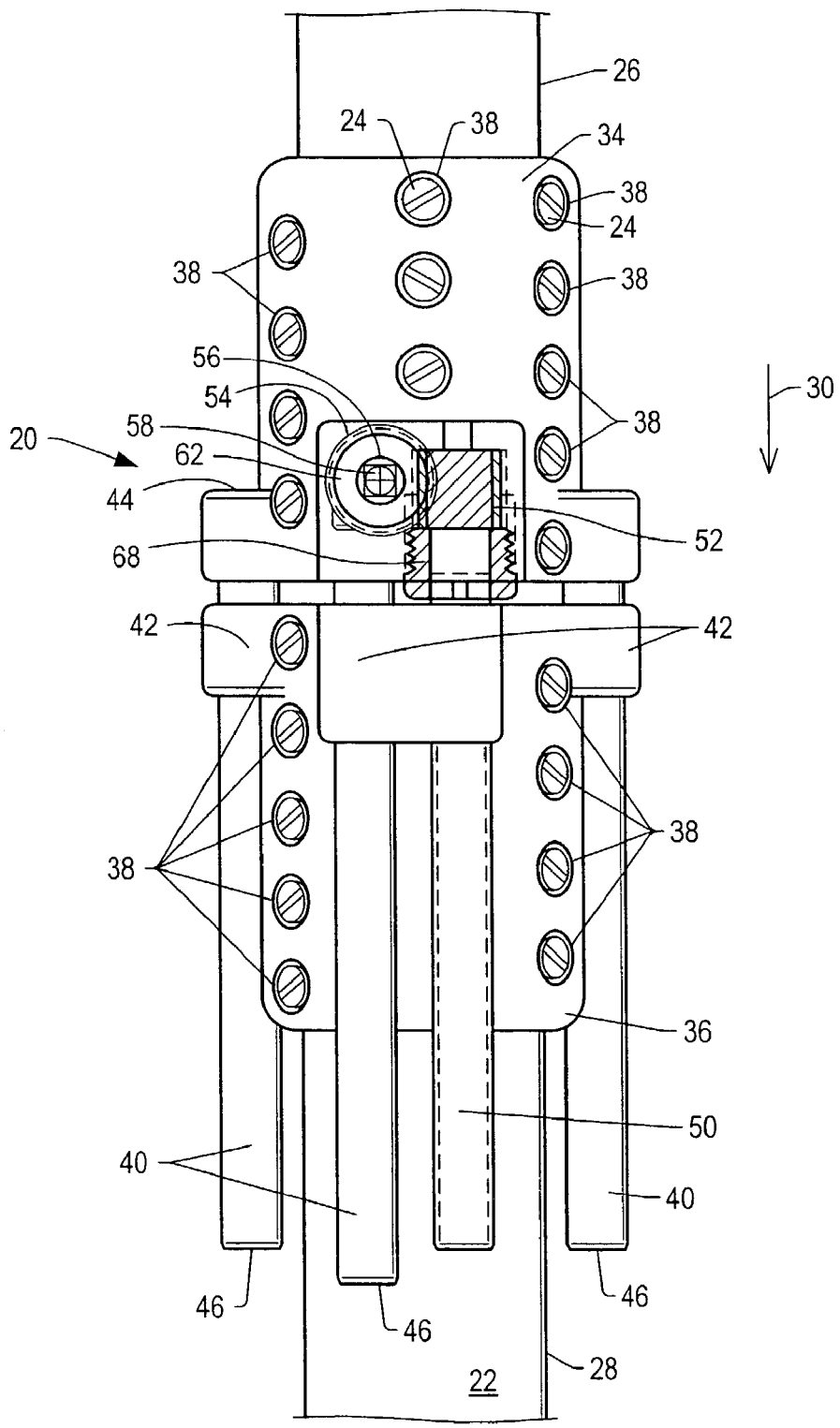
FIG. 1 depicts a representation of an embodiment of a limb lengthener coupled to a bone.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE PREFERRED EMBODIMENTS

Figure 3:
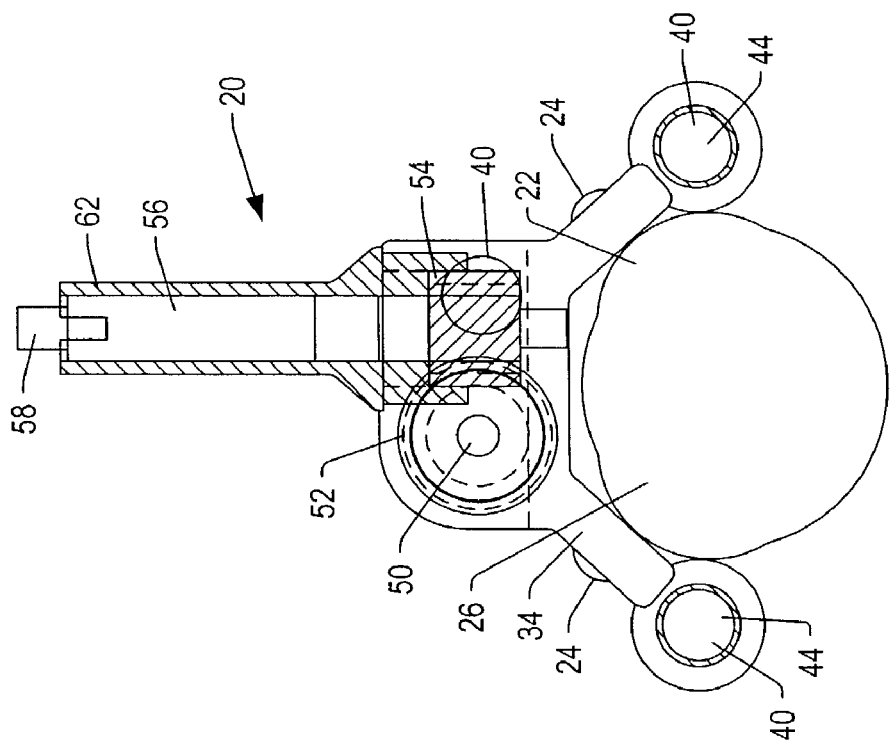
FIG. 3 depicts an end-on representation of another embodiment of a mount of a limb lengthener coupled to a bone segment.
Figure 2:
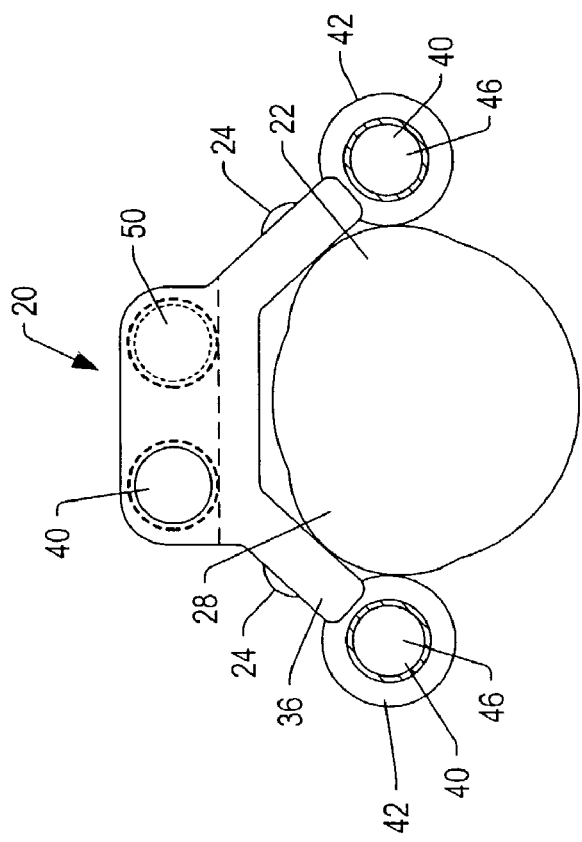
FIG. 2 depicts an end-on representation of an embodiment of a mount of a limb lengthener coupled to a bone segment.

FIG. 1 depicts a representation of an embodiment of limb lengthener 20. Limb lengthener 20 may be used to extend the length of long bone 22. FIG. 1 depicts limb lengthener 20 in an initial position prior to distraction. Limb lengthener 20 may be coupled (e.g., attached or secured) to long bone 22 by fasteners 24, as depicted in FIGS. 2 and 3. Fasteners 24 may be bone screws, nuts and bolts, nails, rivets, trocars, cables, adhesives, or combinations thereof. Fasteners 24 may be received by openings 38 in limb lengthener 20. After coupling limb lengthener 20 to bone 22, the bone may be cut into bone segments 26 and 28. The procedure used to cut bone 22 may be, for example, an osteotomy, surgical corticotomy, or other surgical procedure used to separate a bone into two or more pieces. Bone 22 may be cut such that nerves adjacent to the bone segments are not damaged. In some embodiments, limb lengthener 20 may be coupled to pre-separated bone segments 26 and 28. Bone segments 26, 28 may be pre-separated by a surgical procedure (e.g., before coupling limb lengthener 20 to bone 22, the bone may be cut into first segment 26 and second segment 28) or by a trauma In some embodiments, bone 22 may be partially cut to allow the uncut bone to maintain stability and alignment of first segment 26 relative to second segment 28 during fixation of limb lengthener 20 to the bone. The partially cut bone may serve as a guide for correct placement of limb lengthener 20. After limb lengthener 20 is coupled to bone 22, the bone may be separated into first segment 26 and second segment 28.

After limb lengthener 20 is implanted and bone segments 26, 28 have been separated, the patient's skin may be closed so that an input shaft and/or an input bushing of the limb lengthener extends through the skin. Limb lengthener 20 may be activated without having to reopen the skin to begin distraction of bone 22.

A callus may be allowed to form between bone segments 26, 28. A distractor of the limb lengthener may be activated after formation of the callus to move bone segment 28 in the direction of distraction vector 30. Limb lengthener 20 may be used to gradually distract bone segments 26, 28. Gradual distraction may promote development of the callus between bone segments 26, 28. As bone segments 26, 28 are distracted, the callus may continue to develop between the bone segments. The callus may, after a period of time, be converted to bone by the human body.

As depicted in FIG. 1, limb lengthener 20 may include first mount 34 and second mount 36. First mount 34 and second mount 36 may include openings 38. Openings 38 may receive fasteners 24 to couple first mount 34 and second mount 36 to segments of bone 22. In some embodiments, openings 38 may be threaded to receive fasteners 24. Fasteners 24 may be locking fasteners (e.g., locking screws). In one embodiment, openings 38 are threaded and receive locking fasteners 24. Locking fasteners 24 may secure first mount 34 and second mount 36 to bone segments 26, 28. Threads of locking fasteners 24 may engage first mount 34 and second mount 36 to lock the mounts to limb lengthener 20. In an embodiment, fasteners 24 couple first mount 34 to first bone segment 26 and second mount 36 to second bone segment 28. In one embodiment, first mount 34 and second mount 36 may include five openings 38 each. In another embodiment, first mount 34 and second mount 36 may include nine openings 38 each, as shown in FIG. 1. Fewer or more openings and fasteners may be used in alternate embodiments of mounts 34 and 36 to couple the mounts to bone segments 26 and 28, respectively. In certain embodiments, first mount 34 may have a different number of openings than second mount 36. Bone 22 may be drilled and/or tapped beneath openings 38 before or during an installation procedure. Drilling and/or tapping bone 22 may facilitate coupling of limb lengthener 20 to the bone with fasteners 24. In some embodiments, one or more additional openings 38 and fasteners 24 may be placed at other locations on either first mount 34 and/or second mount 36. These additional openings and fasteners may be used to further secure the first mount and/or the second mount to bone segments.

In an embodiment, limb lengthener 20 includes three or more guide rods 40. Limb lengthener 20 in FIGS. 1-3 shows three guide rods 40 encircling a portion of bone 22. Guide rods 40 may maintain alignment between first mount 34 and second mount 36 as the spacing between the mounts is adjusted during distraction. In some embodiments, fewer or more than three guide rods may be used in a limb lengthener (e.g., a limb lengthener may have 2, 4, 5 or more guide rods).

Openings in first mount 34 may receive first ends 44 of guide rods 40. In certain embodiments, guide rods 40 may be fixedly coupled to first mount 34. The openings in first mount 34 may have a diameter smaller than the diameter of guide rods 40. A tool (e.g., a hammer or similar device) may be used to force guide rods 40 into the openings of first mount 34 to press fit the guide rods into the openings.

Guide rods 40 may be positioned in guides 42 in second mount 36. Guides 42 may have a minimum length based on a relationship between a distance between guide rods 40 and output shaft 50, and the coefficient of friction between the guide rods and the guides. In certain embodiments, a length of guide 42 may be greater than about two times the coefficient of friction times a distance between a center axis of guide rod 40 and a center axis of output shaft 50 as defined in the equation:

$$L > 2 \times u \times D; \tag{1}$$

where L is the length of a guide; u is the coefficient of friction between a guide rod and a guide; and, D is distance between a guide rod and an output shaft.

In certain embodiments, second ends 46 of guide rods 40 may be slidably received in guides 42 of second mount 36 so that the second mount is capable of slidable movement along the guide rods. Guide rods 40 may couple first mount 34 to second mount 36 such that the second mount may move along the path of the guide rods and relative to the first mount. Ends of guide rods 40, or the end of one guide rod, may be re-shaped (e.g., peened) after the guide rods 40 are positioned in guides 42 to inhibit uncoupling of the mounts. In some embodiments, a stop (e.g., a larger diameter end) may be placed at an end of one or more guide rods 40 to inhibit uncoupling of the mounts. Guide rods 40 may allow second mount 36 to move relative to first mount 34 in a controlled path. In an alternate embodiment, guide rods 40 may be fixedly coupled to second mount 36 and may be placed in guides in first mount 34.

In an embodiment, as shown in FIGS. 2 and 3, two guide rods 40 may be positioned adjacent to sides of bone 22 to be lengthened. Another guide rod 40 may be placed adjacent to bone 22 between the other guide rods.

In an embodiment, first mount 34 and second mount 36 move relative to each other to distract separated bone segments 26 and 28. First ends 44 of guide rods 40 may remain in substantially the same position relative to first mount 34 throughout a distraction procedure (i.e., the first ends may be fixedly coupled to the first mount). Second mount 36 may start in a first position (as shown in FIG. 1) and move in the direction of distraction vector 30. Thus, as osteotomized bone segments 26 and 28 are distracted, second mount 36 may move closer to second ends 46 of guide rods 40 relative to its first position. The position of second mount 36 in relation to a point on guide rods 40 changes as bone segments 26 and 28 are distracted.

Bone 22 may be a hand, foot, leg, arm, finger or other suitable bone for use with limb lengthener 20. Lateral stability may be critical for long bones, which are prone to bending and/or twisting during a distraction process. Surrounding a large portion of a circumference of bone 22 with guide rods 40 may enhance the lateral stability of the bone during distraction, thereby substantially decreasing bending moments applied to the bone. Bending moments may be produced by activation of shafts or other moving parts in the limb lengthener. These bending moments may cause misalignment or bending of bone segments in the absence of support such as provided by guide rods 40.

Guide rods 40, along with output shaft 50, may form an arc around bone 22 such that first mount 34 and second mount 36 form an arc around the bone. In certain embodiments, first mount 34 and second mount 36 may form an arc of at least π/3 radians to accommodate the bone circumference. In some embodiments, first mount 34 and second mount 36 may form an arc of at least π radians, at least π/2 radians, at least π/4 radians, at least π/6 radians, or at least π/8 radians. In alternate embodiments, guide rods 40 and output shaft 50 may form a semicircle around bone 22, or may substantially encircle the bone. Encircling bone 22 may allow limb lengthener 20 to have a lower profile and/or held more securely in place. In certain embodiments, one or more of guide rods 40 may be hollow to reduce cost and/or weight of limb lengthener 20.

Figure 5:
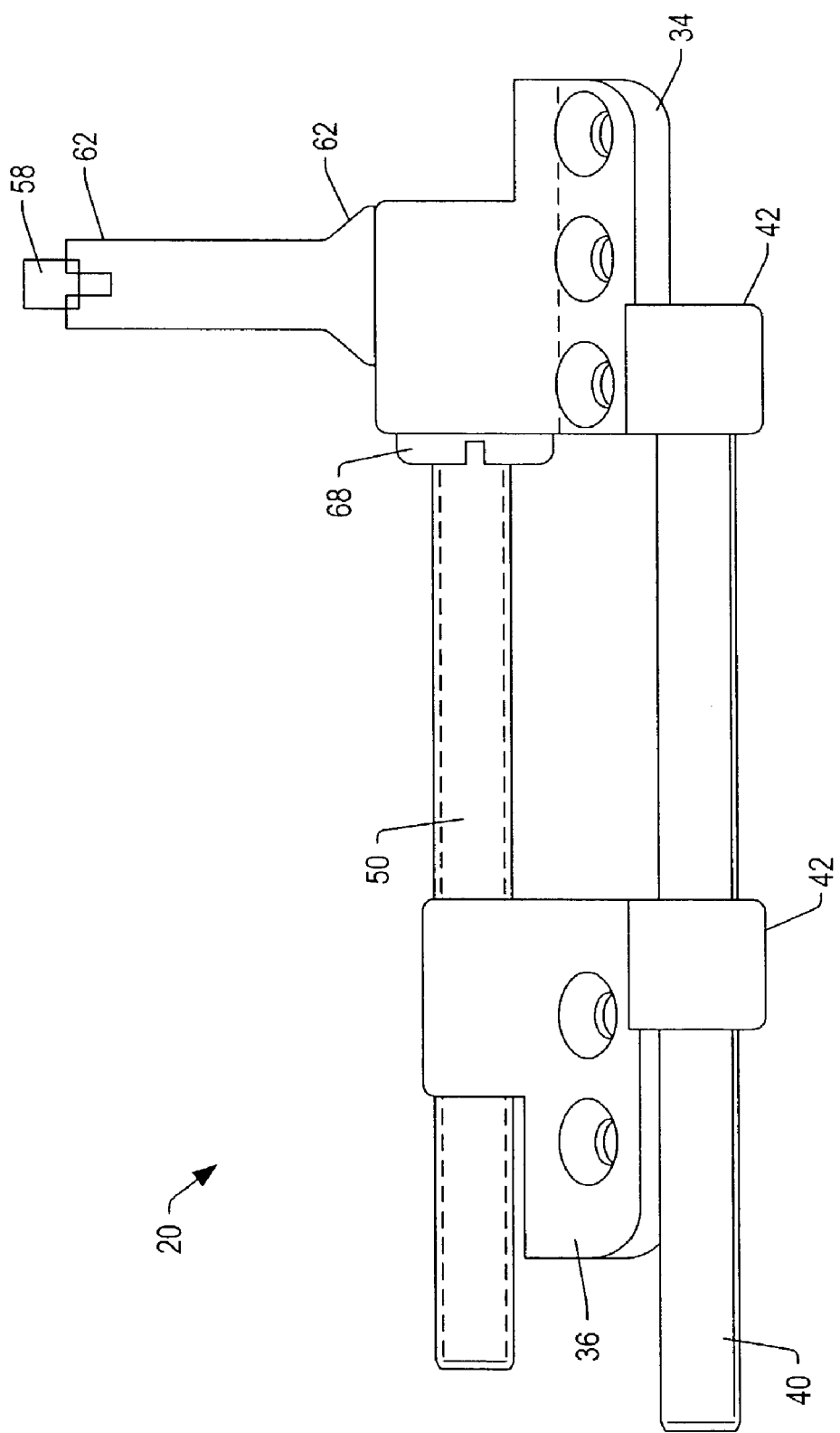
FIG. 5 depicts a representation of an embodiment of a limb lengthener in a mid-distraction position.

Limb lengthener 20 may include a distractor. In an embodiment, the distractor includes output shaft 50 and output gear 52. Output gear 52 of output shaft 50 may be turned by input gear 54. In an embodiment, turning input shaft 56 rotates input gear 54. In certain embodiments, input shaft 56 may be transcutaneous. Input gear 54 may drive output gear 52. Driving output gear 52 may rotate output shaft 50. Output shaft 50 may pass through output bushing 68. Output bushing 68 may allow output shaft 50 to freely rotate in first mount 34 while not allowing significant change in axial position of the output shaft relative to the first mount. Output shaft 50 may include an external thread that mates to a threaded opening in second mount 36. Rotation of output shaft 50 may move second mount 36 relative to first mount 34 as the external thread of the output shaft drives along the threaded opening in the second mount. FIG. 5 depicts a side-on view of an embodiment of limb lengthener 20 with second mount 36 moved away from first mount 34.

Figure 6:
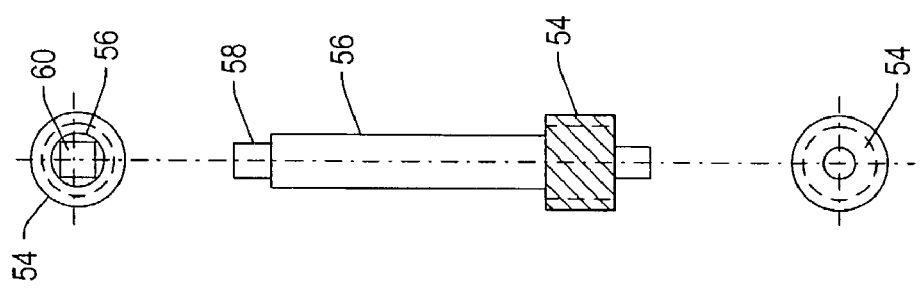
FIG. 6 depicts a side, top, and bottom view of an embodiment of an input shaft.

FIG. 6 depicts an embodiment of input shaft 56. Input shaft 56 may include activation stem 58. Activation stem 58 may interact with an activation device. The activation device may be a tool such as a wrench, screwdriver, ratchet, or other similar tool. Activation stem 58 may, in some embodiments, be a square tip to receive a square head of a wrench, driver, or ratchet. Activation stem 58 may also be shaped as, but not limited to, external or internal polygons such as triangles, hexagons, octagons, dodecagons, or slots, crossed slots, or star patterns. In an embodiment, input shaft 56 may have a length that allows activation stem 58 to extend through a patient's skin while input gear 54 is engaged to an output gear of a limb lengthener. As such, a wrench or other suitable tool may engage tip surface 60 to turn activation stem 58. An activation device may engage activation stem 58 to turn input shaft 56, which in turn activates the limb lengthener input gear. In an embodiment, clockwise rotation of the input shaft allows the second mount to move away from the first mount, and counter clockwise rotation of the input shaft allows the second mount to move towards the first mount.

Figures 7A, 7B:
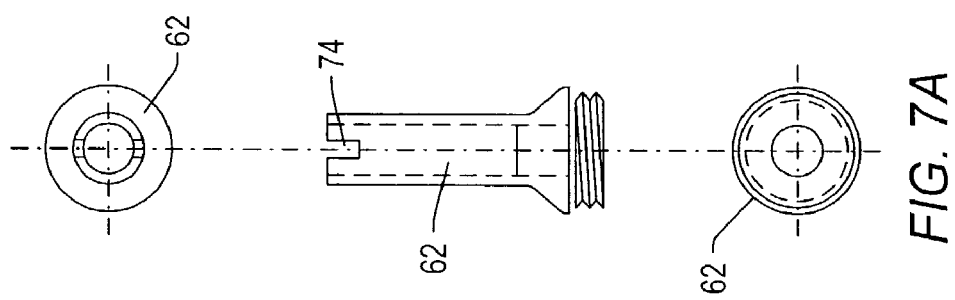
FIG. 7A depicts a side, top, and bottom view of a bushing.
FIG. 7B depicts a cross sectional view of a bushing.

First mount 34 of limb lengthener 20 may have a threaded opening to receive input bushing 62. FIGS. 7A and 7B depict an embodiment of bushing 62. Input shaft 56 of a limb lengthener may extend through an internal cavity of input bushing 62 when the bushing is coupled to the first mount. Input bushing 62 may inhibit removal of the input shaft from an assembled limb lengthener.

Figure 8:
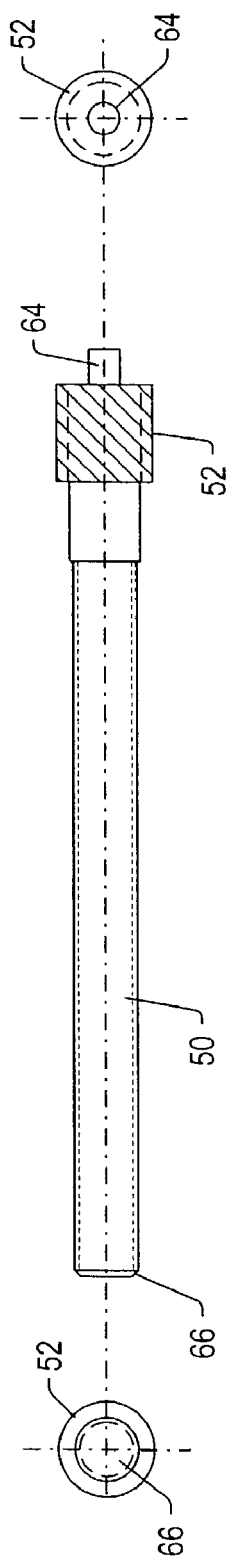
FIG. 8 depicts a side, top, and bottom view of an embodiment of an output shaft.

FIG. 8 depicts an embodiment of output shaft 50 with output gear 52. Output shaft 50 may include first end 64 and second end 66. First end 64 may contact and spin freely in first mount 34 of a limb lengthener. Output shaft 50 may include external threading. An internal opening in second mount 36 of the limb lengthener may receive second end 66 of output shaft 50. The internal opening in the second mount may include threading that mates with the external threading on output shaft 50. When input shaft 56 of the limb lengthener activates input gear 54 that rotates output gear 52 and output shaft 50, the second mount threadably advances along output shaft 50 in a desired direction (e.g., in the direction of distraction vector 30 depicted in FIG. 1 for distraction or, for compression, in the opposite direction of distraction vector 30). The second mount may be displaced with respect to the first mount. The displacement of the second mount may distract bone segments coupled to the first and second mounts of the limb lengthener.

Figure 9:
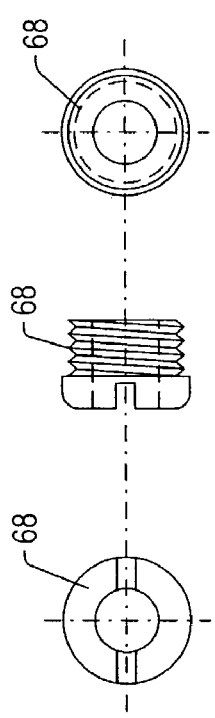
FIG. 9 depicts a side, top, and bottom view of a bushing.

FIG. 9 depicts an embodiment of output bushing 68. Output bushing 68 may couple output shaft 50 of a limb lengthener to first mount 34 of the limb lengthener, as shown in FIG. 1. Output bushing 68 may allow rotation of output shaft 50 without a substantial change in position of the shaft relative to the first mount.

As depicted in FIG. 1, turning activation stem 58 of input shaft 56 in an appropriate direction, depending on the direction of the threading and the direction in which it is desired to move second mount 36 relative to first mount 34, may turn input shaft 56. In an embodiment, turning input shaft 56 causes input gear 54 to engage output gear 52 and cause output shaft 50 to turn. Rotating output shaft 50 may move second mount 36 relative to first mount 34.

Figure 10:
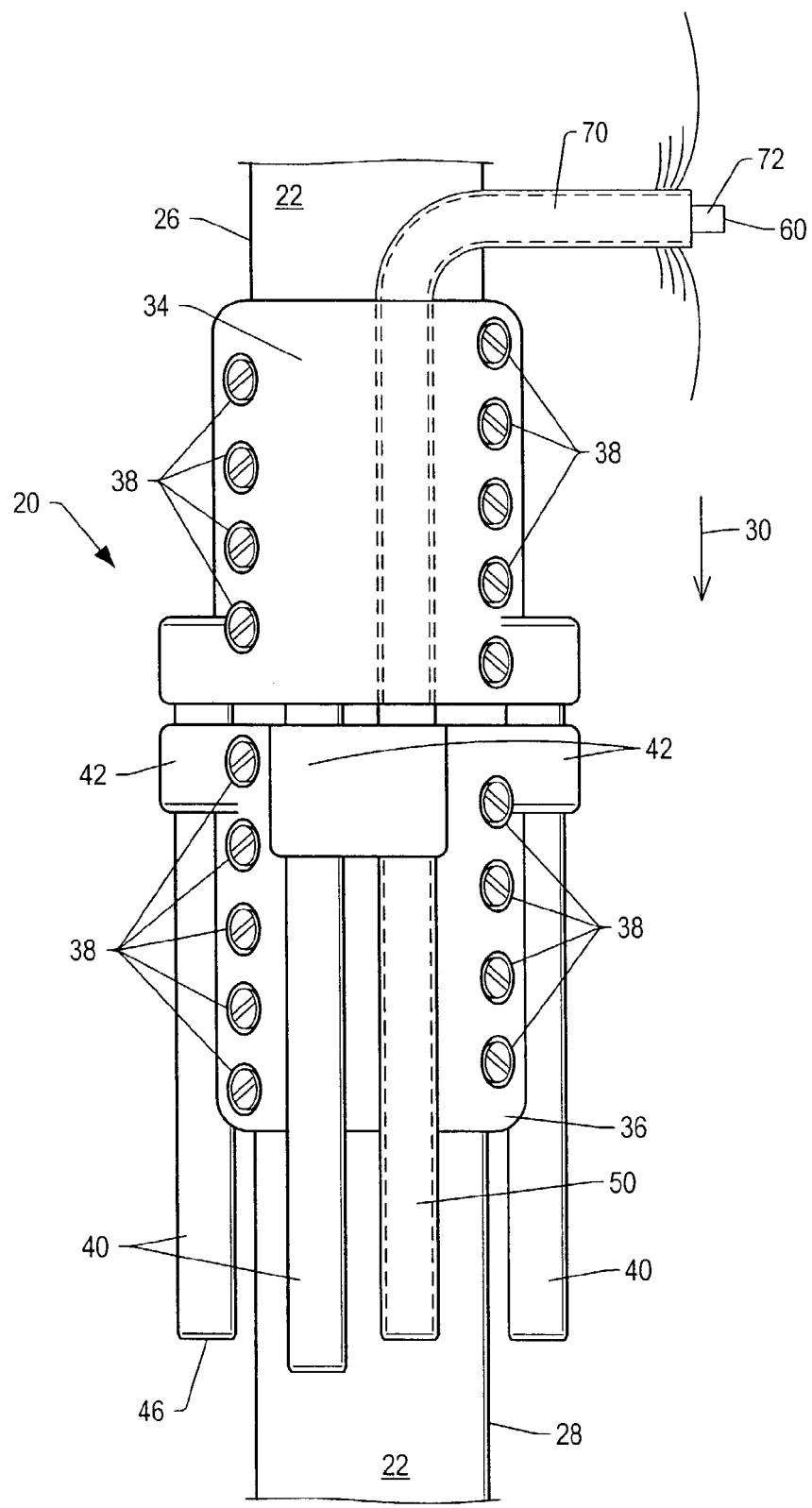
FIG. 10 depicts a representation of an alternate embodiment of a limb lengthener.

In other limb lengthener embodiments, other mechanisms may be used to move the second mount relative to the first mount. For example, FIG. 10 shows sheath 70 and flexible cable 72, which may be used to activate output shaft 50. Cable 72 and sheath 70 may be coupled to output shaft 50 or may be formed as an integral part of the shaft. Cable 72 and sheath 70 may be flexible above first mount 34 to allow the cable and sheath to exit the body of the patient at a desired location away from the first mount. A wrench or other suitable tool may engage tip surface 60 to turn cable 72 to initiate distraction. Sheath 70 may protect adjacent tissue during activation of the device.

In some embodiments, a universal joint system may be used to move a second mount relative to a first mount. A single or double universal joint may engage an input shaft and an output shaft. In certain embodiments, a universal joint may replace an input gear and/or an output gear. Turning an input shaft may drive the universal joint. Driving the universal joint may rotate output shaft. Rotation of the output shaft may move a second mount relative to a first mount as external threading of the output shaft drives along a threaded opening in the second mount. In an embodiment, the output shaft may pass through an output bushing. The output bushing may allow the output shaft to freely rotate in the first mount while not allowing a significant change in axial position of the output shaft relative to the first mount. In an embodiment, the input shaft may be transcutaneous. In some embodiments, the universal joint may be transcutaneous. The universal joint may inhibit removal of the input shaft from an assembled limb lengthener. An input bushing coupled to the universal joint may inhibit removal of the input shaft from an assembled limb lengthener.

As shown in FIG. 1, turning output shaft 50 with respect to second mount 36 may result in displacement of second mount 36 with respect to first mount 34 in a direction parallel to distraction vector 30. First mount 34 may, however, remain stationary relative to distraction vector 30. The displacement of second mount 36 relative to first mount 34 may stretch the bone callus between first osteotomized bone segment 26 and second osteotomized bone segment 28. Stretching (i.e., distracting) the bone callus may encourage generation or promote development of new bone callus. The generation of new bone callus may occur at a faster rate than experienced in normal bone healing. The faster rate may be due in part to the stress applied to the bone by the limb lengthener.

After the desired distraction distance has been achieved, input shaft 56 and input bushing 62 may be removed from the patient. Removal may be accomplished by unscrewing input bushing 62 using a removal tool (e.g., a removal wrench). The removal tool may engage removal slits 74, which are depicted in FIGS. 7A-7B at the top of input bushing 62. For example, input bushing 62 may be removed by turning the removal wrench in a counter-clockwise direction. After input bushing 62 is removed, input shaft 56 may be lifted out of position using pliers or another suitable tool.

After removal of input shaft 56 and/or input bushing 62, a seal and/or a brake may be coupled to limb lengthener 20 to establish, or maintain, the position of output shaft 50. A seal or a brake may engage an input bushing, an input gear, an output gear, and/or a universal joint to inhibit rotation of output shaft 50. Using a seal and/or brake to maintain the position of output shaft 50, may stabilize a distractor after activation.

In an embodiment, after coupling a limb lengthener to bone segments, activation stem 58 may be turned to cause distraction of bone 22. The first turning of the activation stem may be done between zero to about fourteen days after limb lengthener 20 is coupled to the bone segments, or at a time determined by a practitioner as acceptable to avoid complications. The activation stem may be turned periodically (e.g., daily) until bone 22 has been lengthened to a desired length. In an embodiment, one full turn of the activation stem may result in approximately 1 mm of distraction. In other embodiments, one full turn of the activation stem may result in about 2 mm, 3 mm, 4 mm, or larger distances of distraction. FIG. 5 shows an embodiment of limb lengthener 20 in a mid-distraction phase. The practitioner determines the length of distraction necessary based on a discrepancy between the limbs and other factors. In certain embodiments, distraction distances may range from about 0 mm to about 75.0 mm. At the end of distraction, input shaft 56 and input bushing 62 may be removed, while the remainder of limb lengthener 20 may remain in position during a consolidation phase.

In an embodiment, limb lengthener 20 may include an indicator. The indicator may monitor rotation (i.e., activation) of output shaft 50 and/or activation stem. The indicator may include an audible noise and/or a visual display indicating the amount of rotation or activation. Incremental rotations of output shaft 50 and/or activation stem may correlate to incremental changes in the distance of distraction (e.g., one full rotation of an activation stem may correlate to about 1 mm distraction or a partial rotation may correlate to a different amount of distraction). In some embodiments, an indicator may monitor (e.g., register) each activation or partial rotation of output shaft 50 and/or the activation stem (e.g., the indicator may monitor incremental rotation of the output shaft). Indicators may include, but not be limited to, a clicker, a ball spring, and/or a numerical counter.

Figure 11:
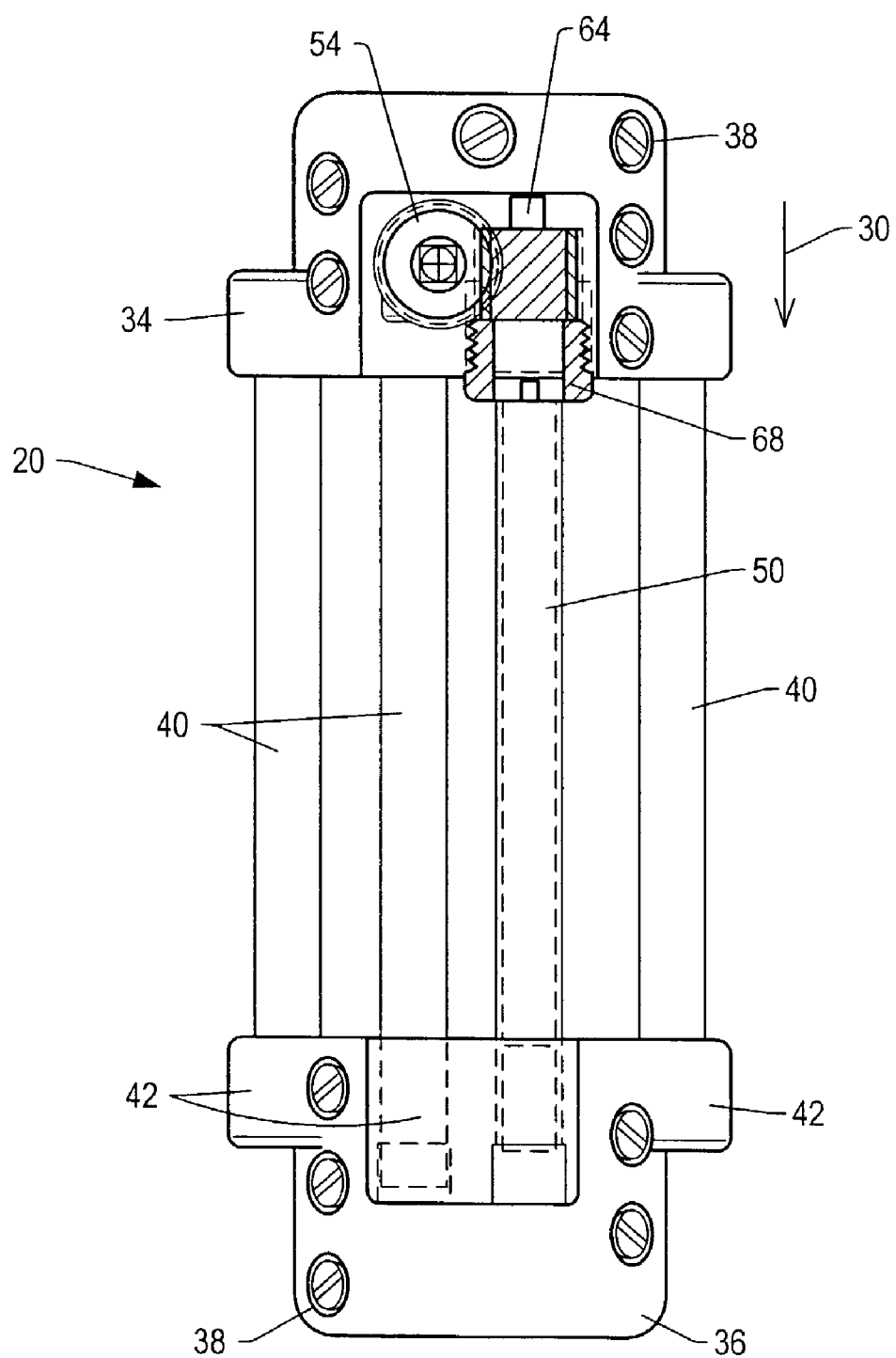
FIG. 11 depicts a representation of an embodiment of a limb lengthener in a post-distraction position.

FIG. 11 shows an embodiment of limb lengthener 20 in a post-distraction phase. The lengths of output shaft 50 and guide rods 40 may be determined by the size of the bone to be distracted and/or the desired distraction distance. Output shaft 50 and guide rods 40 may be provided in various lengths and may be selected and used interchangeably as needed. Alternately, a shaft or rod may be shortened as needed by a practitioner or other user by cutting, sawing, or grinding.

In some embodiments, limb lengthener 20 may remain in place after distraction for a period of from about two to about six months to allow the callus to harden and mature into bone. After a bone has been distracted to the desired length and the callus has hardened satisfactorily, limb lengthener 20 may be removed by removing fasteners 24 from openings 38 of first mount 34 and second mount 36 to disengage the mounts from the bone.

Figure 12:
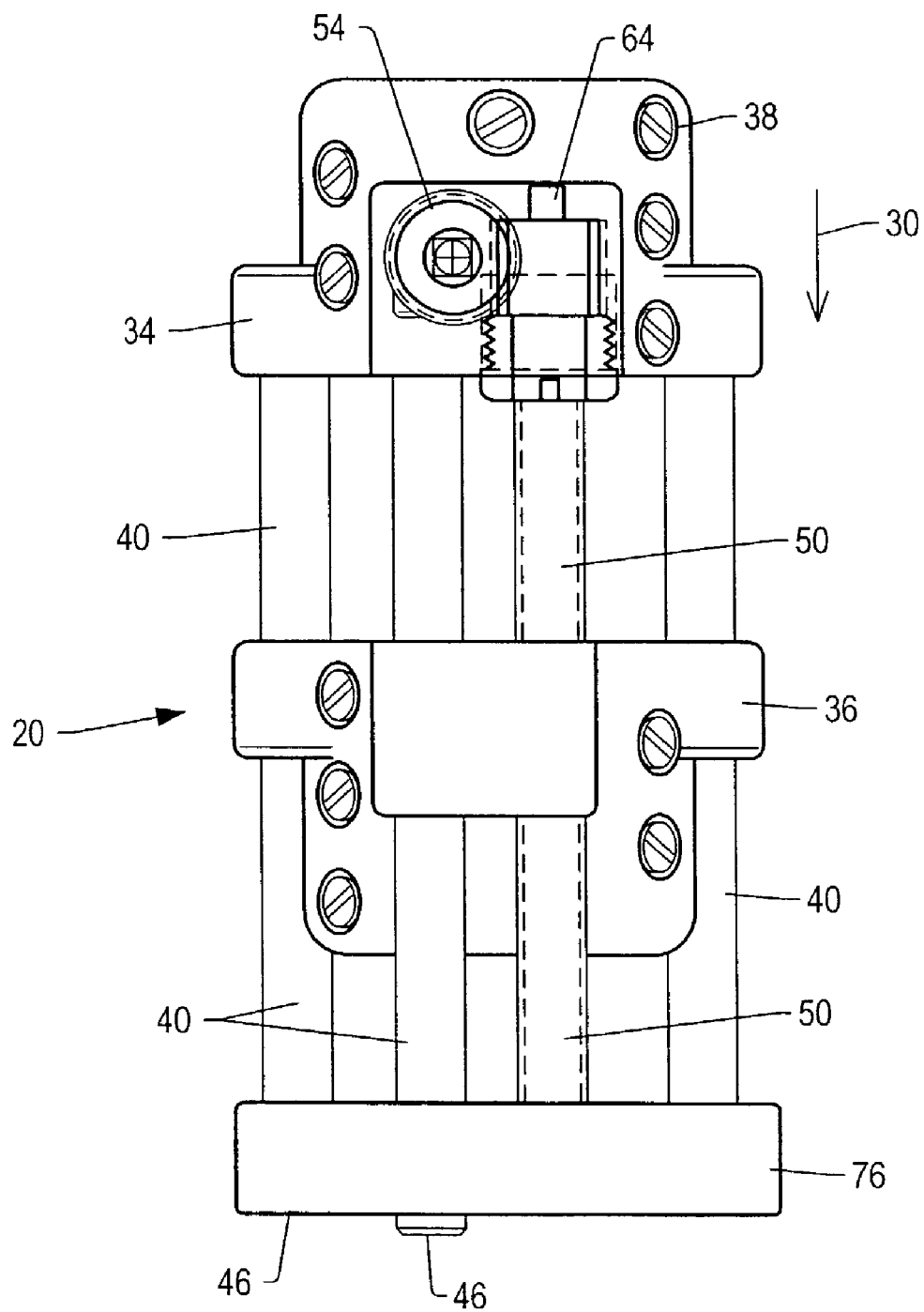
FIG. 12 depicts a representation of an embodiment of a limb lengthener.

FIG. 12 shows an embodiment of limb lengthener 20 that includes third mount 76. Third mount 76 may couple to second ends 46 of guide rods 40 and output shaft 50. Third mount 76 may inhibit relative movement between guide rods 40 and output shaft 50 to improve stability and alignment of device 20. In an embodiment, third mount 76 may be positioned and/or shaped (e.g., curved) so that the third mount does not touch the bone that is being distracted. In some embodiments, an activation mechanism (e.g., an input shaft and/or an output shaft) may be placed in third mount 76. The activation mechanism in third mount 76 may be used either in combination with another activation mechanism or in place of another activation mechanism.

Figure 4:
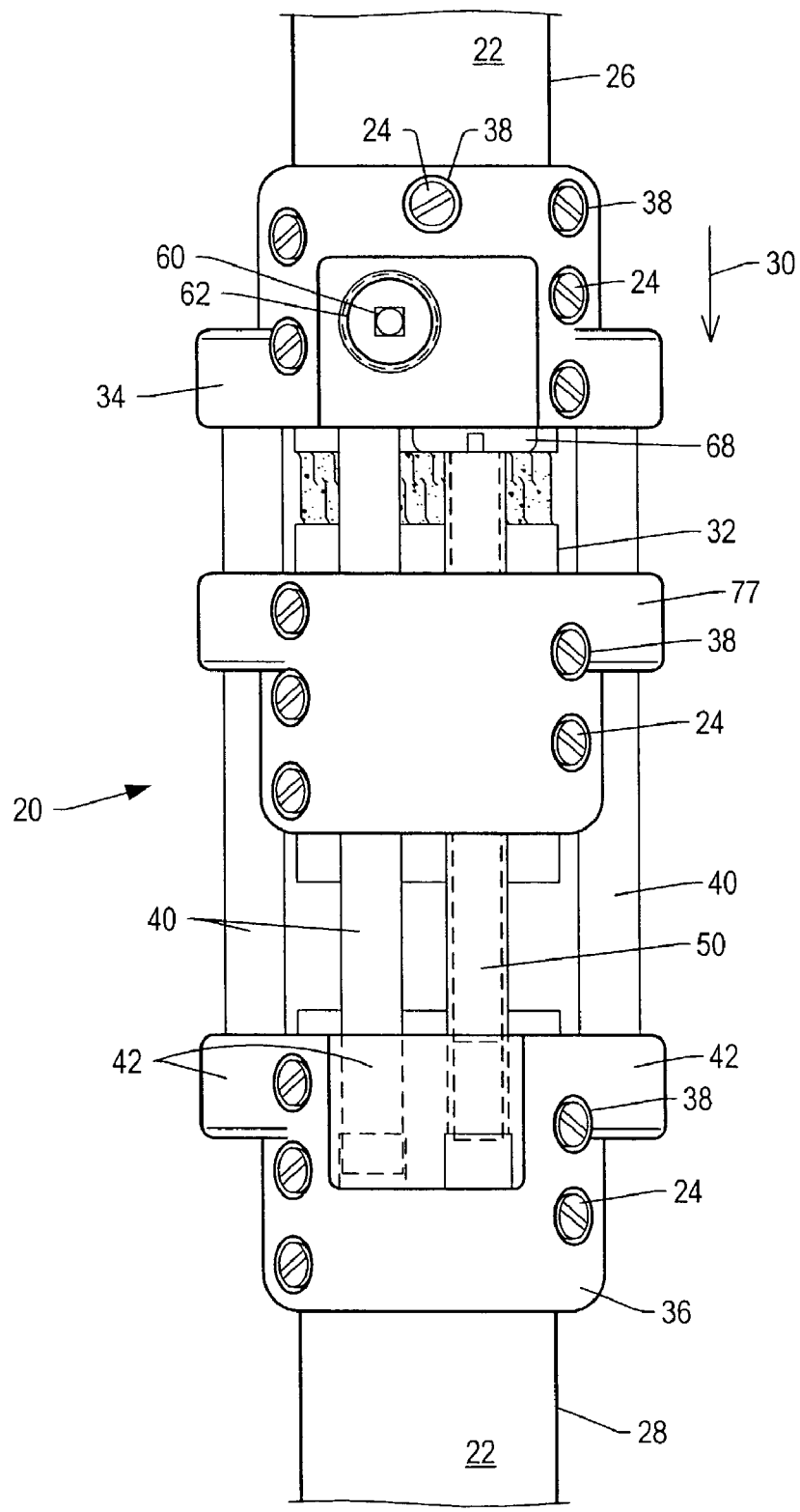
FIG. 4 depicts a representation of another embodiment of a limb lengthener coupled to a bone for transport distraction.

FIG. 4 depicts an alternate embodiment of limb lengthener 20 utilizing transport distraction. Transport distraction may be used where a large initial gap exists in bone 22. The large gap may exist, for example, due to trauma and subsequent surgery, infection and subsequent surgery, or other causes. First mount 34 and second mount 36 may stabilize bone 22. Segment mount 77 may be positioned between first mount 34 and second mount 36 for transport distraction. Segment mount 77 may include openings allowing guide rods 40 and output shaft 50 to pass through the segment mount. An opening in segment mount 77 for output shaft 50 may include threads that mate with the threading on the output shaft. Activation of output shaft 50 may move segment mount 77 relative to first mount 34 and second mount 36 along the path of guide rods 40 and the output shaft.

Transport segment 32 may be coupled to segment mount 77. Transport segment 32 may be a portion of a bone. In some embodiments, transport segment 32 may be obtained by surgically removing a portion of bone segment 26. Alternately, transport segment 32 may be a piece of allograft bone or synthetic bone. Segment mount 77 may be coupled to transport segment 32 between first mount 34 and second mount 36. A callus may be allowed to form between bone segment 26 and transport segment 32. Limb lengthener 20 is activated after formation of the callus to move transport segment 32, coupled to segment mount 77, across the gap between bone segment 26 and bone segment 28 in the direction of distraction vector 30. Transport segment 32 may be distracted until pressed against bone segment 28 to promote healing between the bone segments.

Figure 14:
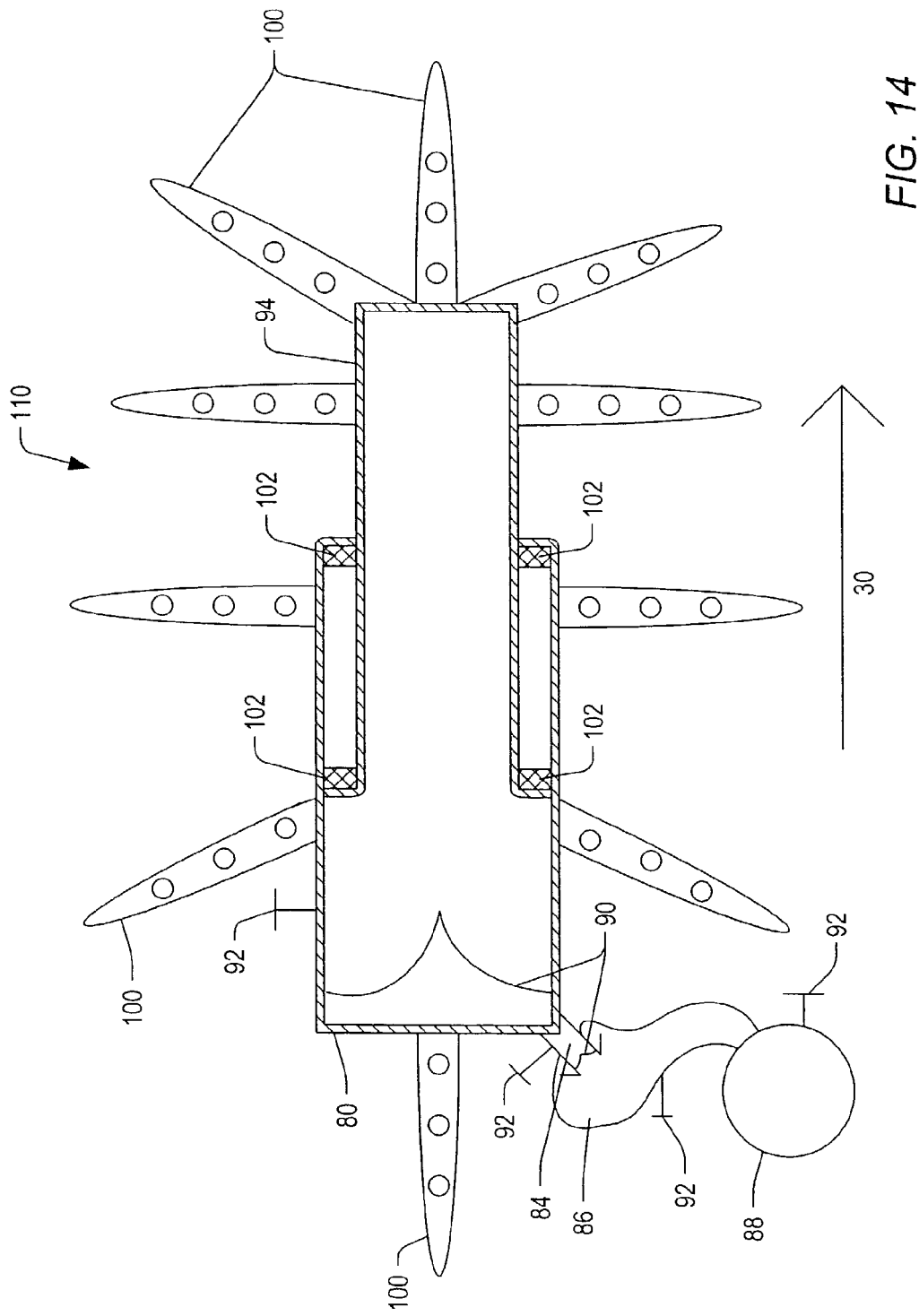
FIG. 14 depicts a cross-sectional representation of an embodiment of a hydraulic bone distractor.

FIG. 14 depicts a representation of an embodiment of hydraulic bone distractor 110. Hydraulic bone distractor 110 may be made of bioabsorbable materials. In certain embodiments, hydraulic bone distractor 110 may include materials such as, but not limited to, poly (D,L-lactide), poly (L-lactide), or other polygycolic acids. For example, hydraulic bone distractor 110 may be made of Lactosorb® obtained from Arthrotek, Inc. (Warsaw, Ind.). An advantage of using a bioabsorbable material is that the patient's body will break down and absorb portions of hydraulic bone distractor 110, eliminating the need for removal of the bone distractor after bone distraction. Hydraulic bone distractor 110 may include hydraulic housing 80. Hydraulic housing 80 may be coupled to a first portion of a bone (e.g., bone segment 26 of bone 22 depicted in FIG. 1). Hydraulic housing 80 may be coupled to the first portion of the bone using one or more plates 100. In an embodiment, plates 100 are break-off plates. Break-off plates may allow flexibility of fitting and coupling of hydraulic bone distractor 110 to bone 22. For example, plates 100 may be broken between the first and second, the second and third openings, and/or any other number of openings away from hydraulic housing 80 and/or piston 94 depending on the size of a bone or the size of the portions of the bone to be distracted. In certain embodiments, hydraulic housing 80 may be shaped to accommodate the circumference of the bone. In alternate embodiments, hydraulic housing 80 may be flexible such that the hydraulic housing may conform to the shape of the bone upon coupling to the bone. In some embodiments, hydraulic housing 80 may be coupled to first mount 34, which is coupled to bone 22 (as depicted in FIG. 1).

Hydraulic bone distractor 110 may include piston 94. Piston 94 may be at least partially enclosed in hydraulic housing 80. Piston 94 may be coupled to a second portion of the bone (e.g., bone segment 28 of bone 22 depicted in FIG. 1). Piston 94 may be coupled to the second portion using plates 100. In some embodiments, piston 94 may be coupled to second mount 36, which is coupled to bone 22 (as depicted in FIG. 1).

Seals 102 may be used to enclose a portion of piston 94 in hydraulic housing 80 to inhibit the escape of fluid from the hydraulic housing. In an embodiment, seals 102 are o-ring seals that surround the circumference of piston 94. During use, seals 102 may allow for movement of piston 94 relative to hydraulic housing 80 while stabilizing the piston in the hydraulic housing and inhibiting the escape of fluid.

Pump 88 may be coupled to hydraulic housing 80. In some embodiments, conduit 86 may couple pump 88 to hydraulic housing 80. Connector 84 may be used to couple conduit 86 to hydraulic housing 80. Pump 88 may be located subcutaneously or outside of the body. Conduit 86 may have a length that varies depending on a location of pump 88 relative to hydraulic housing 80. If pump 88 is located subcutaneously, the pump, conduit 86, and connector 84 may be made of bioabsorbable materials. In an embodiment, pump 88 is a syringe type device, which may be operated either internally or externally. In some embodiments, pump 88 may be battery powered. Pump 88 may be used to provide a hydraulic fluid to hydraulic housing 80. The hydraulic fluid may be any biocompatible fluid used to provide pressure in hydraulic housing 80. In an embodiment, the hydraulic fluid is saline fluid.

Pump 88 may provide hydraulic fluid into hydraulic housing 80 for distraction of bone portions. The provided hydraulic fluid may provide a force against the portion of piston 94 enclosed in hydraulic housing 80 so that the piston moves relative to the hydraulic housing (i.e., the piston is pushed out of the hydraulic housing in the direction of distraction vector 30). As more hydraulic fluid is provided to hydraulic housing 80, piston 94 may be further pushed out of the hydraulic housing. Moving piston 94 relative to hydraulic housing 80 causes distraction of the second portion of the bone coupled to the piston relative to the first portion of the bone coupled to the hydraulic housing.

Valve 90 may inhibit backflow of hydraulic fluid from hydraulic housing 80 towards pump 88. In an embodiment, valve 90 is a one-way valve. Valve 90 may be placed in hydraulic housing 80 and/or in connector 84, as shown in FIG. 14.

In an embodiment, pump 88 is charged (pre-loaded) with a selected amount of hydraulic fluid. The amount of hydraulic fluid may be selected to provide a desired distance of distraction between the bone portions. Pump 88 may discharge hydraulic fluid in an elastic or spring like manner, which provides a constant force against piston 94 and, thus, a constant rate of distraction. The rate of distraction may be controlled or selected to allow time for regrowth of bone tissue during distraction. In certain embodiments, the force required for distraction may be relatively small (e.g., between about 4 pounds and 10 pounds). In some embodiments, the force required to achieve distraction may be less for a hydraulic distractor than other mechanical types of distractors. In addition, a hydraulic distractor may apply force substantially a direction of distraction with relatively little or no torsional or bending components.

In some embodiments, one or more bleed valves 92 may be coupled to hydraulic housing 80, connector 84, conduit 86, and/or pump 88. Bleed valves 92 may be used to relieve excess pressure in hydraulic housing 80. Bleed valves 92 may remove excess fluid that may cause unwanted distraction of the bone and/or compression of the bone.

Figure 13:
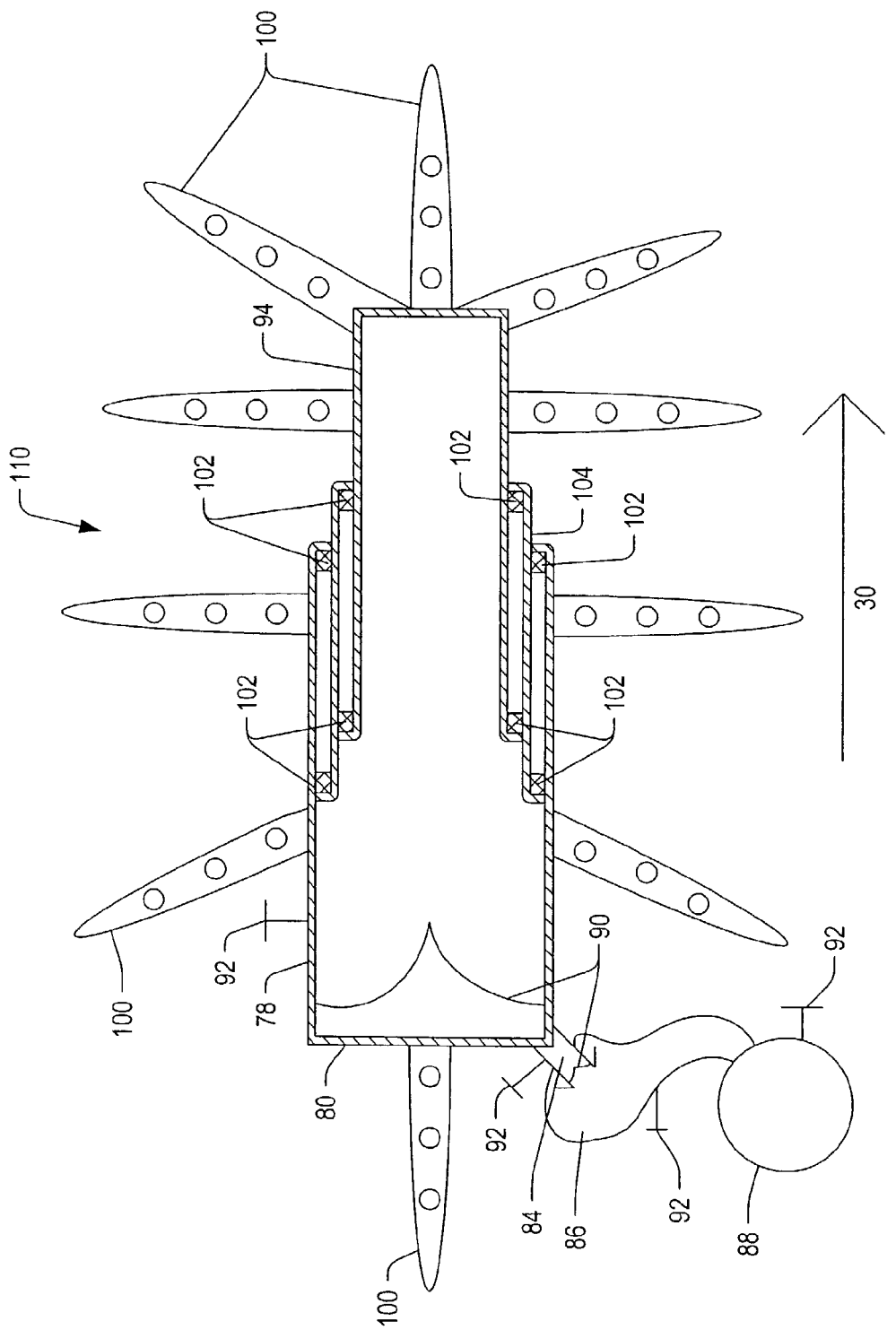
FIG. 13 depicts a cross-sectional representation of an embodiment of a hydraulic bone distractor.

FIG. 13 depicts another embodiment of hydraulic bone distractor 110. Hydraulic bone distractor 110 may include intermediate hydraulic cylinder 104. Intermediate hydraulic cylinder 104 may be at least partially enclosed in hydraulic housing 80. Piston 94 may be partially enclosed in intermediate hydraulic cylinder 104. Seals 102 may enclose a portion of intermediate hydraulic cylinder 104 in hydraulic housing 80 and a portion of piston 94 in the intermediate hydraulic cylinder.

In an embodiment, hydraulic fluid provided into hydraulic housing 80 provides a force against the portion of piston 94 in the hydraulic housing and intermediate hydraulic cylinder 104 to move the piston relative to the intermediate hydraulic cylinder. Piston 94 may be continually pushed out of intermediate hydraulic cylinder 104 with the addition of more hydraulic fluid until the piston is fully extended from the intermediate hydraulic cylinder. After full extension of piston 94, the further addition of hydraulic fluid provides a force against the piston and intermediate hydraulic cylinder 104 so that the intermediate hydraulic cylinder moves relative to hydraulic housing 80 (i.e., the intermediate hydraulic cylinder is pushed out of the hydraulic housing). Movement of piston 94 and intermediate hydraulic cylinder 104 relative to hydraulic housing 80 may cause distraction of a bone segment coupled to the piston from a bone segment coupled to the hydraulic housing. Using intermediate hydraulic cylinder 104 in hydraulic bone distractor 110 may allow for a smaller hydraulic bone distractor to be used for a given distraction distance. The telescoping effect of using intermediate hydraulic cylinder 104 and piston 94 allows for increased distraction distance compared to a similarly sized hydraulic bone distractor without the intermediate hydraulic cylinder.

In certain embodiments, other structures may be employed as a distractor. Some embodiments may contain distractors that allow controllable, incremental movement of output shaft 50 through second mount 36. An example of such a distractor may be a ratcheting arrangement that includes one or more notches on an output shaft that interact with a projection or tooth on a ratcheting mechanism to control movement. In some embodiments, a small solenoid type motor may be used to supply motive forces to a distractor. The small motor may be placed internally and controlled externally with conventional remote control technology.

In some embodiments, surfaces of a limb lengthener that contact bone may be treated to promote osteointegration. The treatment may include, but is not limited to, applying a titanium plasma spray to selected surfaces, applying a hydroxyapatite coating to selected surfaces, and/or texturing selected surfaces. In an embodiment, a limb lengthener may be formed of medical grade stainless steel (e.g., 316L stainless steel) and/or a titanium-aluminum alloy (e.g., $Ti_6Al_4V$-Eli).

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A bone distraction device, comprising:
   a first mount configured to be subcutaneously coupled to a first portion of a bone, wherein the first mount is contoured in an arc of at least $\pi/3$ radians to accommodate the circumference of the bone;
   a second mount configured to be subcutaneously coupled to a second portion of the bone, wherein the second mount is contoured in an arc of at least $\pi/3$ radians to accommodate the circumference of the bone;
   three or more guide rods, wherein a first end of each guide rod is coupled to the first mount, and wherein each of the guide rods is coupled to the second mount; and
   a distractor coupled to the first and second mounts, wherein the distractor is configured to subcutaneously move the second mount relative to the first mount during use such that the second portion of the bone is distracted from the first portion of the bone, wherein the distractor comprises an output shaft, the output shaft configured to subcutaneously rotate, and when rotated, the output shaft is configured to move the second mount relative to the first mount; and
   a transcutaneous actuator configured to transcutaneously engage the output shaft such that turning the transcutaneous actuator rotates the output shaft while the output shaft is subcutaneously disposed.

2. The device of claim 1, wherein the second mount is configured to move relative to the first mount along an axis parallel to the longitudinal axis of the three or more guide rods during use.

3. The device of claim 1, wherein at least two of the guide rods are configured to be positioned substantially 180° apart along the circumference of the bone.

4. The device of claim 1, wherein the first mount and the second mount comprise fastening means for coupling to the bone.

5. The device of claim 1, wherein the first mount and the second mount are configured to be fastened to the bone using screws.

6. The device of claim 1, wherein the first mount and the second mount are configured to be coupled to the bone using locking fasteners.

7. The device of claim 1, further comprising locking fasteners, wherein locking fasteners engage the first mount and the second mount, and wherein the locking fasteners secure the first mount and the second mount to the bone.

8. The device of claim 1, wherein the first mount further comprises one or more first openings, wherein the second mount further comprises one or more second openings, and wherein the first openings and the second openings are configured to receive locking fasteners.

9. The device of claim 1, wherein at least one of the guide rods is hollow.

10. The device of claim 1, wherein the first end of each guide rod is configured to be fixably coupled to the first mount.

11. The device of claim 1, wherein each of the guide rods is configured to slidably pass through an opening in the second mount during use.

12. The device of claim 1, wherein one of the guide rods is positioned in a guide, and wherein a length of the guide is greater than about two times a coefficient of friction between the guide and the guide rod, times the distance between a center axis of the guide rod and a center axis of the output shaft.

13. The device of claim 1, wherein the output shaft comprises a first end configured to be coupled to the first mount, and a second threaded end configured to be threadably received by the second mount.

14. The device of claim 1, wherein the output shaft comprises an output gear.

15. The device of claim 14, wherein the output gear is configured to turn the output shaft during use to move the second mount along the second threaded end of the output shaft.

16. The device of claim 1, wherein the transcutaneous actuator includes a universal joint coupled to the output shaft, wherein the universal joint is configured to extend outside a body of a patient at a desired location.

17. The device of claim 1, wherein the transcutaneous actuator includes a flexible cable, the flexible cable configured to transcutaneously couple to the output shaft.

18. The device of claim 17, wherein the flexible cable is configured to turn the output shaft during use to move the second mount along the second threaded end of the output shaft.

19. The device of claim 17, wherein the flexible cable is placed in a sheath.

20. The device of claim 1, wherein the transcutaneous actuator includes an input shaft, wherein the input shaft is configured to engage the output shaft such that turning the input shaft rotates the output shaft during use.

21. The device of claim 20, further comprising a brake, wherein the brake is configured to maintain a position of the output shaft when the input shaft is removed.

22. The device of claim 20, further comprising a seal, wherein the seal is configured to maintain a position of the output shaft when the input shaft is removed.

23. The device of claim 20, wherein the input shaft comprises an activation stem and an input gear.

24. The device of claim 23, wherein rotation of the activation stem rotates the input gear during use.

25. The device of claim 23, wherein the output shaft comprises an output gear, and wherein the input gear is configured to engage the output gear during use.

26. The device of claim 23, further comprising an indicator configured to monitor activation of the output shaft.

27. The device of claim 23, wherein one full rotation of the activation stem is configured to distract bone segments a predetermined distance during use.

28. The device of claim 23, wherein one full rotation of the activation stem is configured to distract bone segments about 1.0 mm during use.

29. The device of claim 23, wherein the activation stem is configured to engage an activation device, and wherein turning the activation device activates distraction during use.

30. The device of claim 1, wherein the device comprises bioabsorbable materials.

31. The device of claim 1, wherein the device comprises titanium.

32. The device of claim 1, wherein the device comprises aluminum.

33. The device of claim 1, wherein the device comprises steel.

34. The bone distraction device of claim 1, wherein the distractor is directly coupled to the first and second mounts.

35. The device of claim 1, wherein the three or more guide rods are configured to substantially surround the circumference of the bone.

36. A method of lengthening a bone of a patient, comprising:
    making an osteotomy in the bone to form a first portion of the bone and a second portion of the bone; and
    separating the second portion of the bone from the first portion of the bone using a distraction device subcutaneously coupled to the bone, the distraction device comprising a distractor, wherein the distractor is coupled to a first and second mounts, and wherein the distractor moves the second mount relative to the first mount along three or more guide rods, wherein the first mount is subcutaneously coupled to the first portion of the bone and the second mount is subcutaneously coupled to the second portion of the bone, and wherein the first mount and the second mount are contoured in an arc of at least $\pi/3$ radians to accommodate the circumference of the bone; wherein the distractor includes a subcutaneously disposed output shaft, and wherein rotation of the output shaft moves the second mount relative to the first mount; and
    rotating of the output shaft using an actuator that transcutaneously extends from the output shaft to outside the skin of the patient.

37. The method of claim 36, wherein the distractor is directly coupled to the first and second mounts.

38. A method of installing and using a bone distraction device to lengthen a bone of a patient, comprising:
    making an osteotomy in the bone to form a first portion of the bone and a second portion of the bone;
    coupling a distraction device subcutaneously to the bone, the distraction device comprising a distractor, wherein the distractor is coupled to a first and second mounts, and wherein the distractor enables the second mount to move relative to a first mount along three or more guide rods, wherein the first mount is coupled to the first portion of the bone and the second mount is coupled to the second portion of the bone, and wherein the first mount and the second mount are contoured in an arc of at least $\pi/3$ radians to accommodate the circumference of the bone; wherein the distractor includes a subcutaneously disposed output shaft, and wherein rotation of the output shaft moves the second mount relative to the first mount;
    separating the second portion of the bone from the first portion of the bone using an actuator that transcutaneously extends from the output shaft to outside the skin of the patient.

39. The method of claim 38, wherein the distractor is directly coupled to the first and second mounts.

40. A bone distraction device, comprising:
    a first mount configured to be coupled to a first portion of a bone, wherein the first mount is contoured in an arc of at least $\pi/3$ radians to accommodate the circumference of the bone;
    a second mount configured to be coupled to a second portion of the bone, wherein the second mount is contoured in an arc of at least $\pi/3$ radians to accommodate the circumference of the bone;
    a third mount configured to be coupled to a bone portion, wherein the third mount is contoured in an arc of at least $\pi/3$ radians to accommodate the circumference of the bone portion, and wherein the third mount is configured to be placed between the first mount and the second mount;
    three or more guide rods, wherein a first end of each guide rod is configured to be coupled to the first mount and a second end of each guide rod is configured to be coupled to the second mount, and wherein each of the guide rods is configured to pass through an opening in the third mount; and
    a distractor configured to move the third mount relative to the first mount and the second mount during use such that the bone portion is distracted from the first portion of the bone towards the second portion of the bone.

41. The device of claim 40, wherein the bone portion comprises an allograft bone.

42. The device of claim 40, wherein the bone portion comprises a synthetic bone.

43. The device of claim 40, wherein the bone portion is configured to be compressed against the second portion of bone during use.

44. The device of claim 40, wherein the third mount is configured to move relative to the first mount and the second mount along an axis parallel to the longitudinal axis of the three or more guide rods during use.

45. The device of claim 40, wherein at least two of the guide rods are configured to be positioned substantially 180° apart along the circumference of the bone.

46. The device of claim 40, wherein the first mount, the second mount, and the third mount comprise fastening means for coupling to the bone.

47. The device of claim 40, wherein the first mount, the second mount, and the third mount are configured to be fastened to the bone using screws.

48. The device of claim 40, wherein at least one of the guide rods is hollow.

49. The device of claim 40, wherein the first end of each guide rod is configured to be fixably coupled to the first mount.

50. The device of claim 40, wherein the second end of each guide rod is configured to be fixably coupled to the second mount.

51. The device of claim 40, wherein each of the guide rods is configured to slidably pass through an opening in the third mount during use.

52. The device of claim 40, wherein the distractor comprises an output shaft.

53. The device of claim 52, wherein one of the guide rods is positioned in a guide, and wherein a length of the guide is greater than about two times a coefficient of friction between the guide and the guide rod, times the distance between a center axis of the guide rod and a center axis of the output shaft.

54. The device of claim 52, wherein the output shaft comprises a first end configured to be coupled to the first mount, a second end configured to be coupled to the second mount, and a threaded portion configured to be threadably received by the third mount.

55. The device of claim 52, wherein the output shaft comprises an output gear.

56. The device of claim 55, wherein the output gear is configured to turn the output shaft during use to move the third mount along the threaded portion of the output shaft.

57. The device of claim 52, further comprising a flexible cable coupled to the output shaft.

58. The device of claim 52, further comprising a universal joint coupled to the output shaft.

59. The device of claim 57, wherein the flexible cable is configured to turn the output shaft during use to move the third mount along the threaded portion of the output shaft.

60. The device of claim 57, wherein the flexible cable is configured to extend outside a body of a patient at a desired location.

61. The device of claim 57, wherein the flexible cable is placed in a sheath.

62. The device of claim 52, further comprising an input shaft, wherein the input shaft is configured to engage the output shaft such that turning the input shaft rotates the output shaft during use.

63. The device of claim 62, further comprising a seal, wherein the seal is configured to maintain a position of the output shaft when the input shaft is removed.

64. The device of claim 62, further comprising a brake, wherein the brake is configured to maintain a position of the output shaft when the input shaft is removed.

65. The device of claim 62, wherein the input shaft comprises an activation stem and an input gear.

66. The device of claim 65, wherein rotation of the activation stem rotates the input gear during use.

67. The device of claim 65, wherein the output shaft comprises an output gear, and wherein the input gear is configured to engage the output gear during use.

68. The device of claim 65, wherein one full rotation of the activation stem is configured to distract bone segments a predetermined distance during use.

69. The device of claim 65, wherein one full rotation of the activation stem is configured to distract bone segments about 1.0 mm during use.

70. The device of claim 65, further comprising an indicator configured to monitor activation of the activation stem.

71. The device of claim 65, wherein the activation stem is configured to engage an activation device, and wherein turning the activation device activates distraction during use.

72. The device of claim 40, wherein the device comprises bioabsorbable materials.

73. The device of claim 40, wherein the device comprises titanium.

74. The device of claim 40, wherein the device comprises aluminum.

75. The device of claim 40, wherein the device comprises steel.

76. A method of lengthening a bone, comprising:
   inserting a bone portion between a first portion of the bone and a second portion of the bone; and
   distracting the bone portion from the first portion of the bone towards the second portion of the bone using a distraction device coupled to the bone, the distraction device comprising a distractor configured to move a third mount relative to a first mount and a second mount along three or more guide rods, wherein the first mount is coupled to the first portion of the bone, the second mount is coupled to the second portion of the bone, and the third mount is coupled to the bone portion, and wherein the first mount, the second mount, and the third mount are contoured in arcs of at least $\pi/3$ radians to accommodate the circumference of the bone.

77. A method of installing and using a bone distraction device to lengthen a bone, comprising:
   coupling a distraction device to the bone, the distraction device comprising a distractor configured to move a third mount relative to a first mount and a second mount along three or more guide rods, wherein the first mount is coupled to a first portion of the bone, the second mount is coupled to a second portion of the bone, and the third mount is coupled to a bone portion, and wherein the first mount, the second mount, and the third mount are contoured in an arc of at least $\pi/3$ radians to accommodate the circumference of the bone; and
   distracting the bone portion from the first portion of the bone towards the second portion of the bone using the distraction device.

* * * * *